United States Patent [19]

DiGiovanni et al.

[11] 4,430,997
[45] Feb. 14, 1984

[54] MULTIPLE CLIP APPLIER

[75] Inventors: John DiGiovanni, Irvington; Donald M. Golden, Cherry Hill, both of N.J.

[73] Assignee: Ethicon, Inc., Somerville, N.J.

[21] Appl. No.: 208,368

[22] Filed: Nov. 19, 1980

[51] Int. Cl.³ .............................................. A61B 17/12
[52] U.S. Cl. .................................... 128/326; 128/325; 227/DIG. 1
[58] Field of Search .................... 128/325, 326, 334 R; 227/19, DIG. 1; 29/243.56

[56] References Cited

U.S. PATENT DOCUMENTS

| D. 253,611 | 12/1979 | Jarvik et al. | 128/334 R |
| 4,166,466 | 9/1979 | Jarvik | 128/325 |
| 4,296,751 | 10/1981 | Blake et al. | 128/325 |
| 4,316,468 | 2/1982 | Klieman et al. | 128/325 |
| 4,325,376 | 4/1982 | Klieman et al. | 128/325 |

Primary Examiner—C. Fred Rosenbaum
Assistant Examiner—C. W. Shedd
Attorney, Agent, or Firm—Donal B. Tobin

[57] ABSTRACT

An apparatus for housing, feeding and applying multiple ligating clips, including a handle which houses a delivery and feeding mechanism, and a cartridge which holds the clips. The handle employs a scissors-type action to set a clip which has been delivered to the jaws by the feeding and ratcheting mechanism. The feeding mechanism provides a relatively long stroke motion to deliver a clip from the end of a cartridge to the end of the nose. The mechanism also provides a relatively short stroke motion for operating the ratchet mechanism of the cartridge for feeding clips through the cartridge. The feeding, ratcheting and setting of the clip is all done by a single, scissors-type action employing only a small motion envelope so that the overall shape of the handle may be small and compact and readily adaptable for use deep in an incision site. The cartridge includes a fixed and moving ratchet rack which are operated by the short stroke ratcheting mechanism of the handle. Clips are fed from the end of the ratchet into the nose of the handle by a delivery means which may either push the clip into the nose or physically hold and carry the clip into the nose. The delivery device is driven by the long stroke delivery action of the handle. The entire apparatus may be disposable or the handle may be a reusable item adapted for use with disposable cartridges.

15 Claims, 11 Drawing Figures

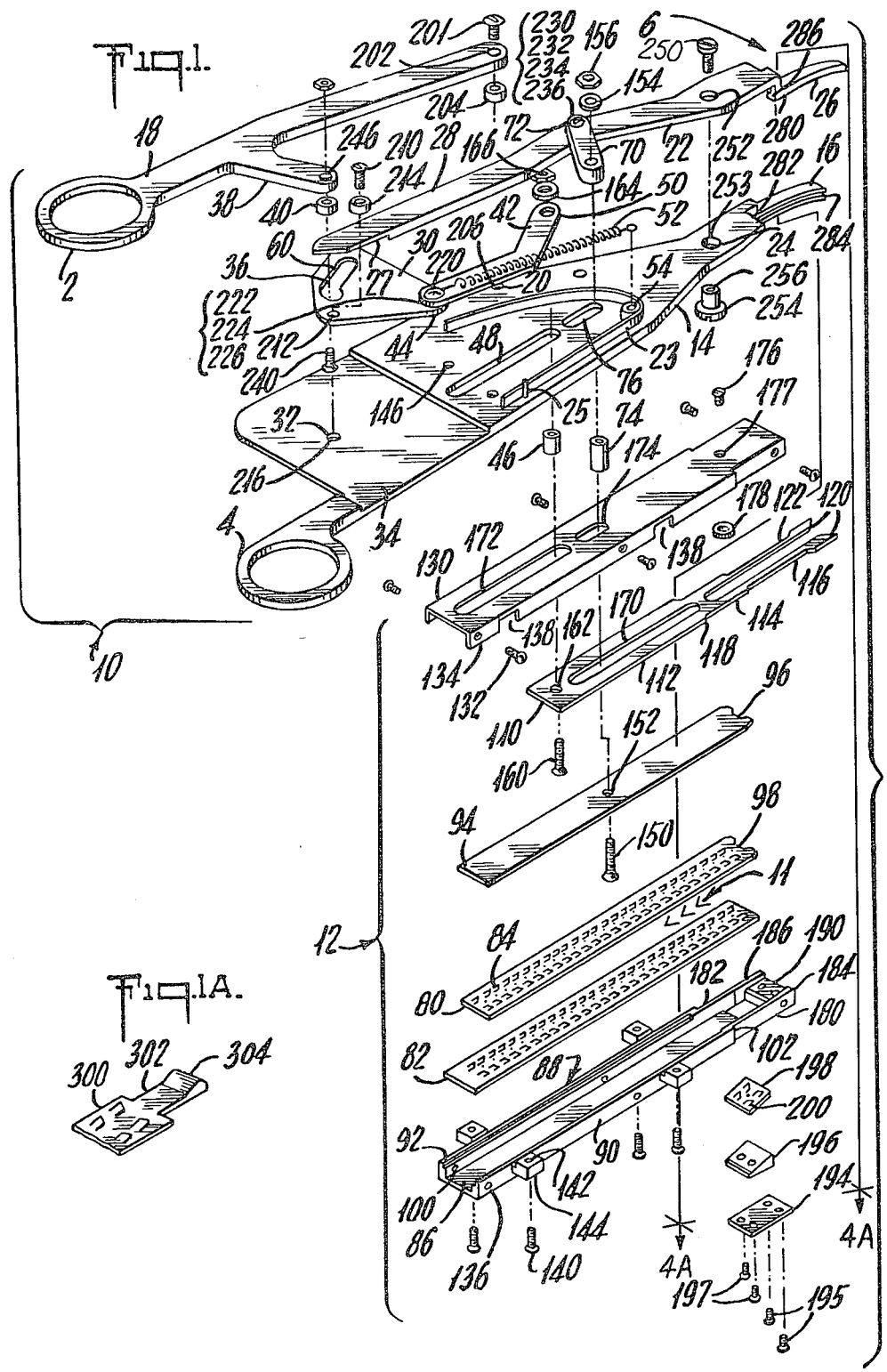

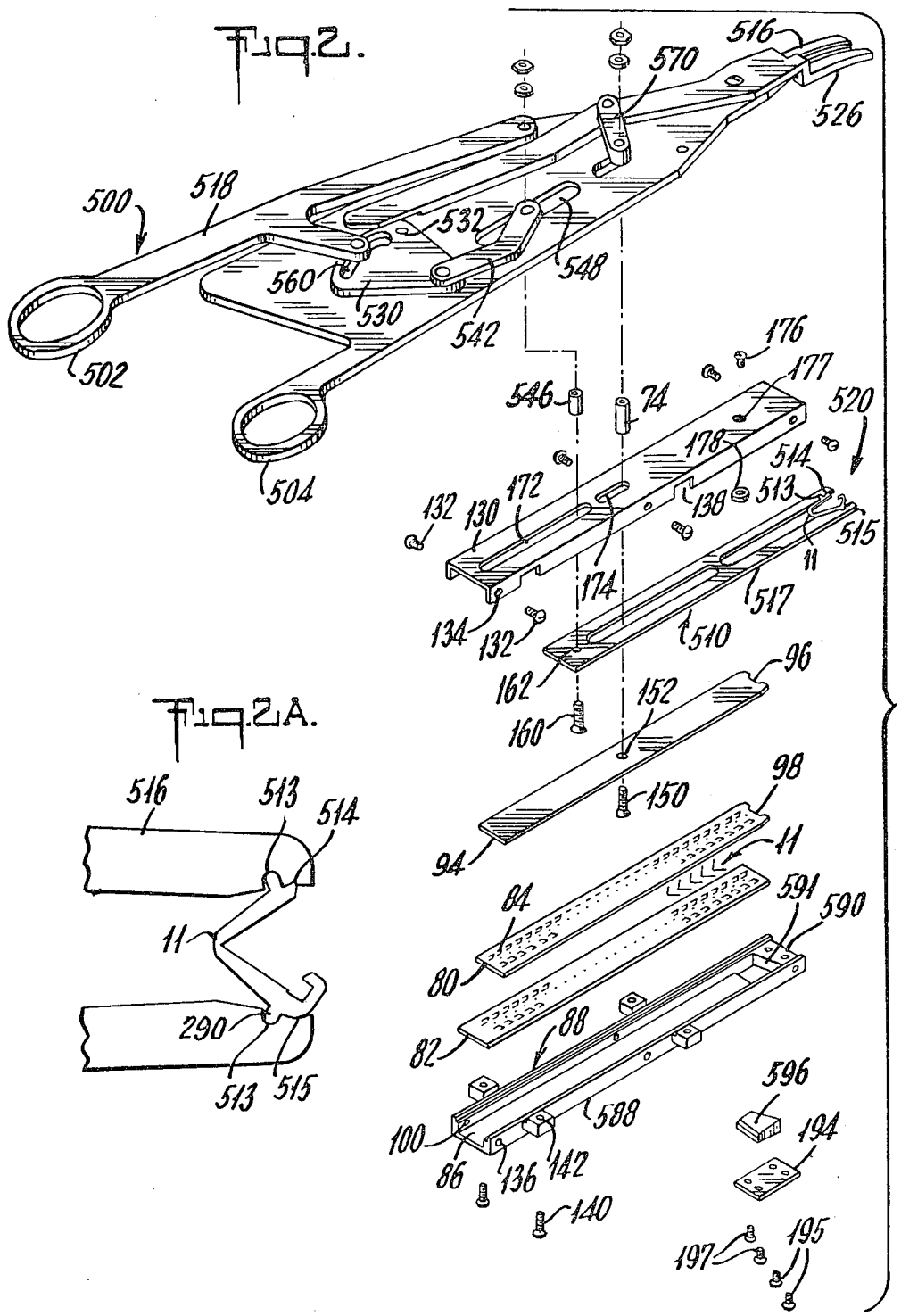

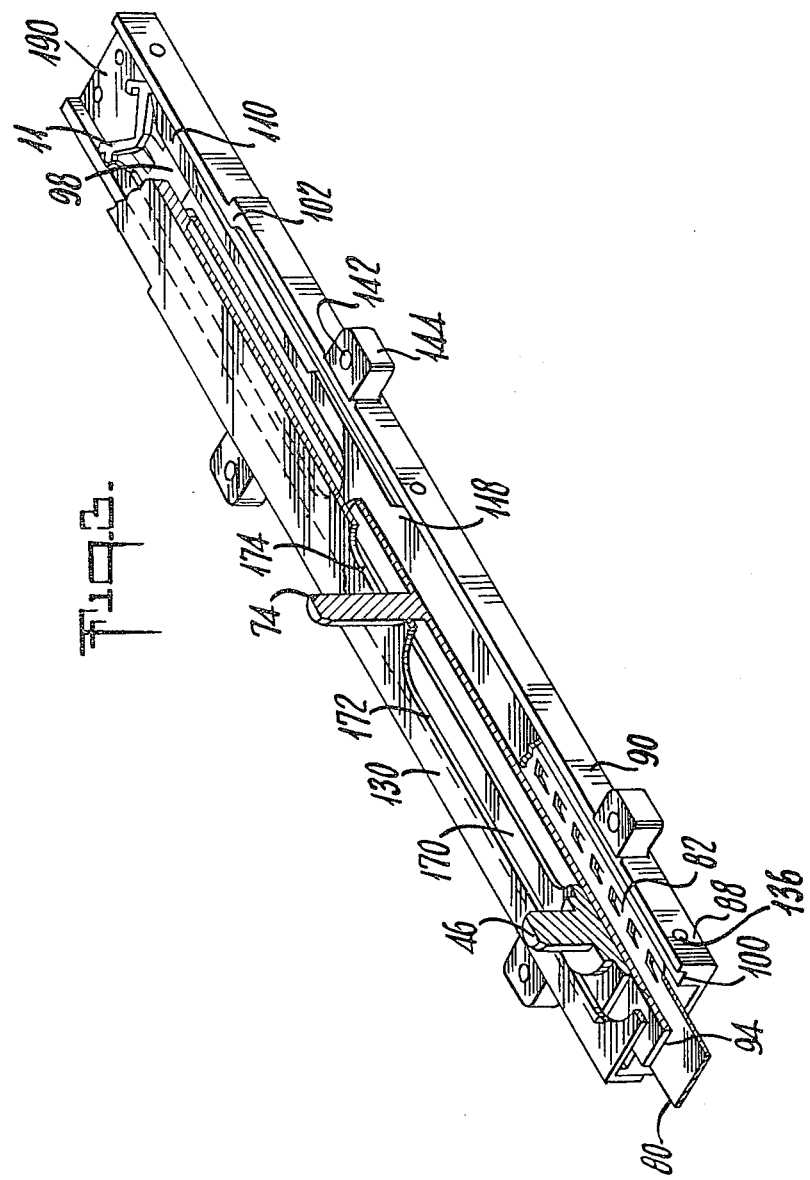

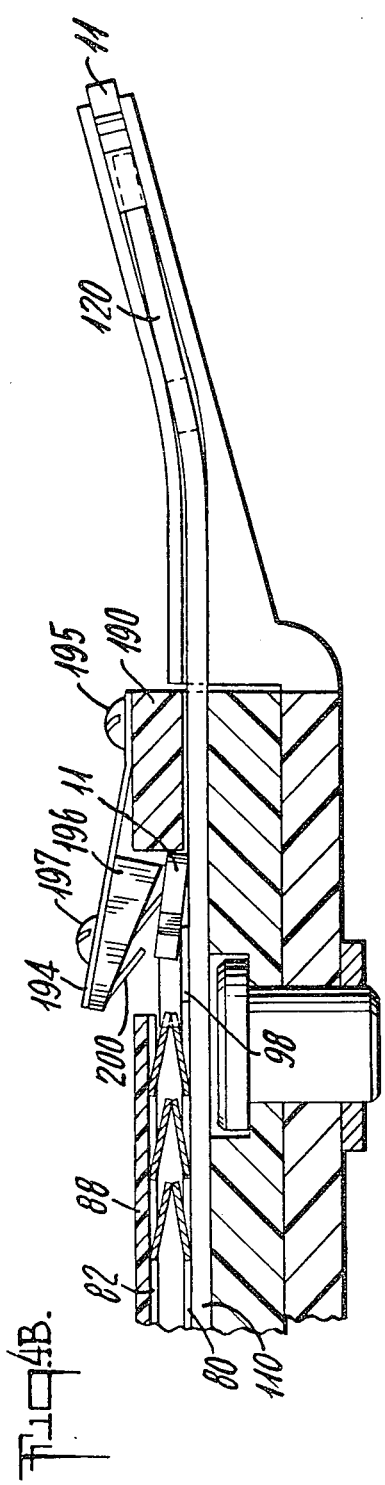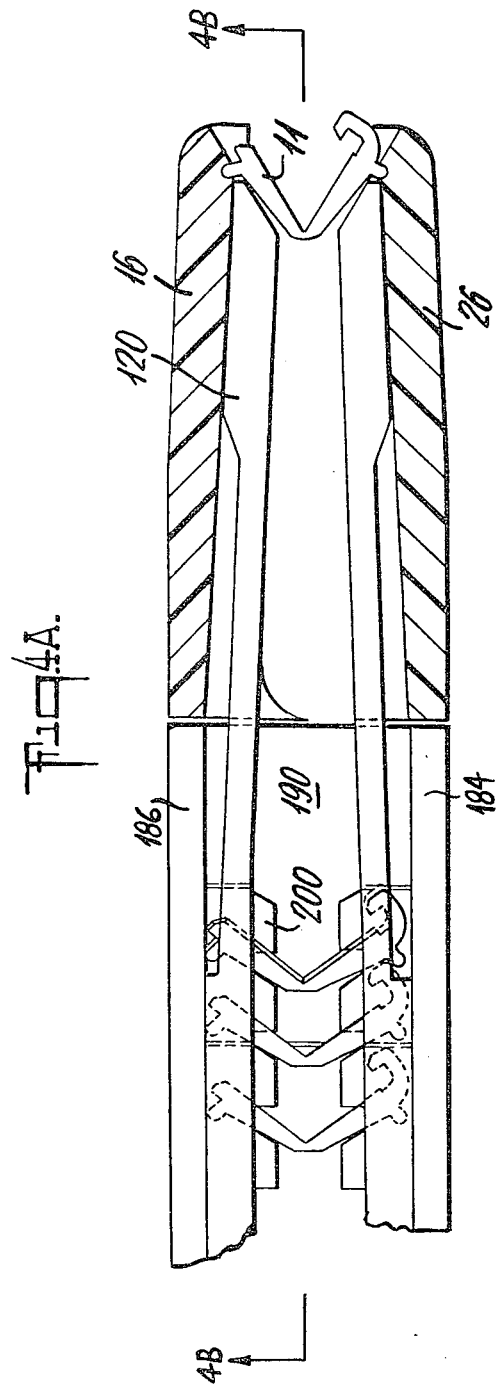

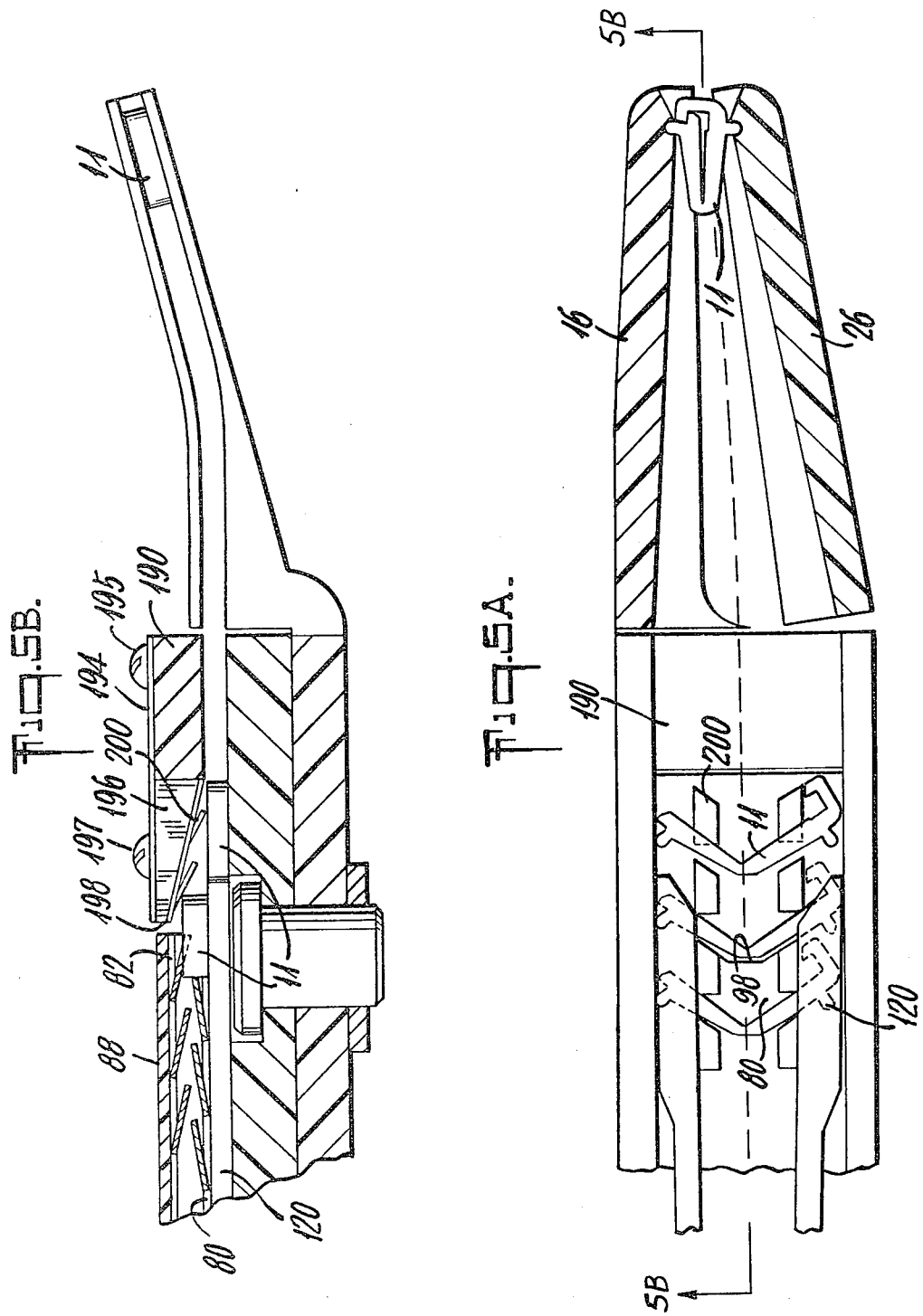

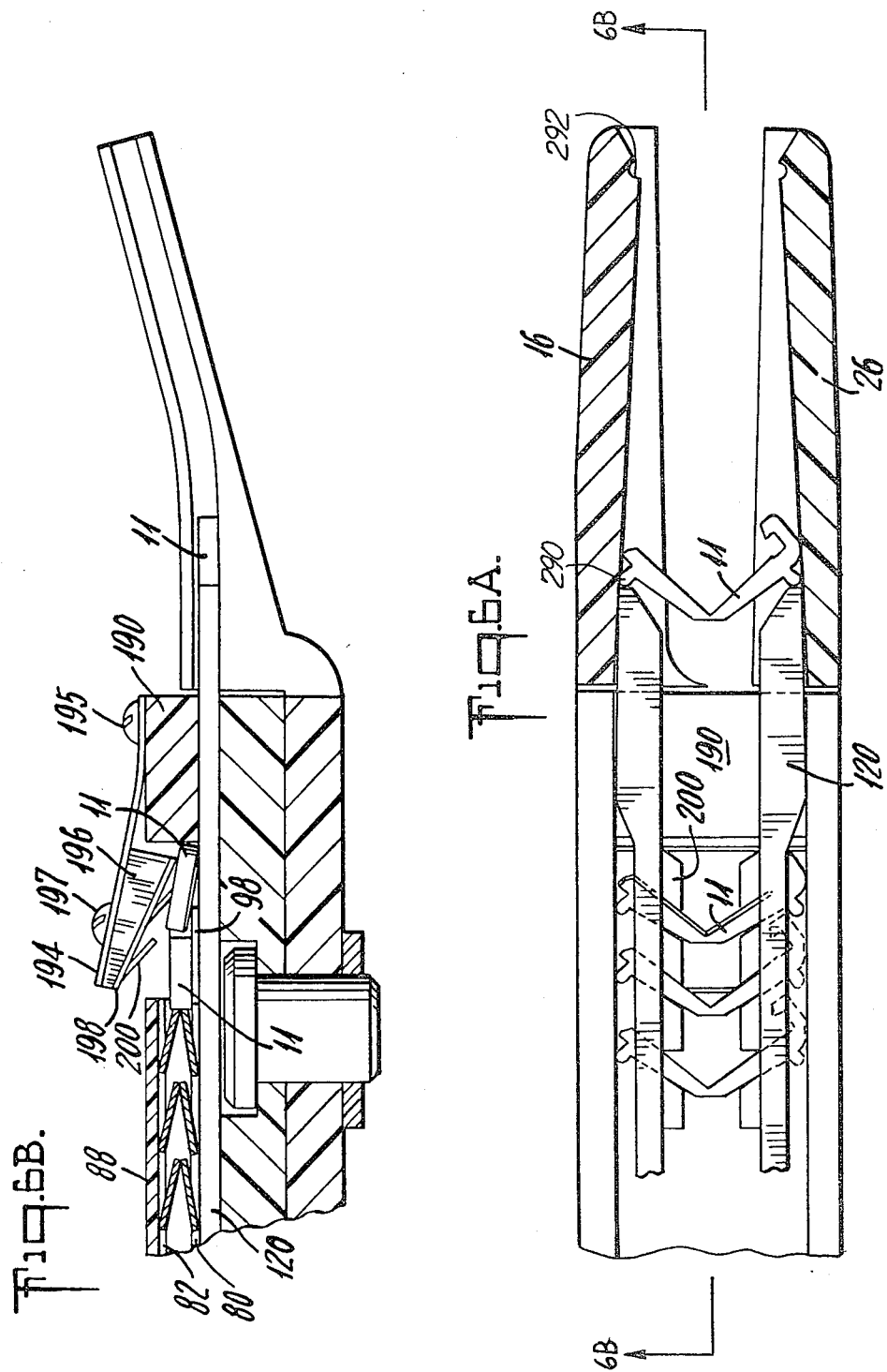

MULTIPLE CLIP APPLIER

BACKGROUND OF THE INVENTION

The present invention relates to an apparatus for applying surgical clamps and clips and more particularly to a multiple clip applier.

In the past, when surgeons wished to cut a blood vessel, they would commonly suture it in two places spaced a short distance along the vessel and then cut between the sutures. Even for a skilled surgeon, the manipulations required to place two sutures about a vessel and then tie and cut the sutures can be time consuming. In recent years, the practice of using metal or plastic clips to ligate a vessel has gained increasing acceptance. Instead of suturing a vessel in two places, a surgeon need only apply two clips to the vessel and then cut between the clips. In many instances, the clips are applied one at a time as shown, for example, in U.S. Pat. No. 3,713,533. A clip is removed from a clip holder, loaded into the jaws of a clip applier and then the loaded applier is inserted into the ligation site and the clip is applied. Although this provides a perfectly satisfactory ligating technique, it can be slow because time is required to load the individual clips and to transfer them into the operating site for application.

Attempts have been made to provide a multiple clip applier where the applier itself supports a cartridge of many clips. The devices shown in U.S. Pat. No. 2,874,384 employ a multiple clip cartridge placed on the end of an auxiliary arm attached to the pivot point of an ordinary hemostat. Although such devices may provide satisfactory results, the user is required to place two fingers in the ring holes and close the hemostat about a vessel to be ligated. The auxiliary arm is then operated by a third finger while the hemostat is still held by the user. The applier must be rotated into position and compressed to set a clip about the vessel. This is a difficult and slow motion which many surgeons may find uncomfortable to use.

In the multiple stapler shown in U.S. Pat. No. 3,082,426, one must close the rings of the scissors-type hemostat part way to hold the vessel. One must then slide a staple advance mechanism forward with one's index finger while holding the rings of the hemostat with one's thumb and third finger until the staple advances into the hemostat jaws surrounds the vessel. The user then continues to close the hemostat jaws to set the staple about the vessel.

The multiple clamp appliers shown in U.S. Pat. No. 2,968,041 use a pistol-grip action where clips are applied by jaws at the end of a long-barrelled instrument operated by a pistol-grip handle at the other end of the instrument. Other devices have used a syringe-type action where the user pushes a plunger with his thumb through a barrel on the end of which is supported an anvil for collapsing the staple about the vessel. See, for example, U.S. Pat. No. 3,079,608.

Still other units use a pump-action motion where the vessel is held in the jaws of a hemostat and the staple is advanced and set about the vessel by sliding a staple cartridge along the hemostat body. See, for example, U.S. Pat. No. 3,592,377.

It is desirable to have a multiple clip applier that may be operated with one hand using the familiar scissors action of a hemostat. The total envelope of the scissors motion should be small so that the instrument may be comfortably operated without unusual manipulations. The small envelope of motion permits the instrument to be used in the confined space of a surgical incision. The normal scissors action of a hemostat provides good motor control for the surgeon while he is placing the clip about the vessel to be ligated and while he is closing the clip to seal off the vessel. It is desirable to have a large magazine of clips so that the surgeon does not have to change cartridges during an operation. There should be enough clips to permit the surgeon to discharge clips at the beginning of the operation to make sure that he is using with the correct type and size of clip. It is desirable to avoid motions which require the surgeon to use both hands to apply a clip or which require awkward manipulation of some of the fingers while other fingers are holding a ring-type instrument. Such manipulations may tire the surgeon and also extend the operating time. It is also desirable to have an instrument which may be inexpensively manufactured so that the entire device could be disposable, to eliminate the expense of cleaning and sterilizing an instrument and to avoid the hazard of cross-infection from an improperly sterilized instrument.

SUMMARY OF THE INVENTION

The present invention provides a multiple clip applier with a large cartridge of clips removably affixed to a scissors-type handle. The handle houses a mechanism for delivering clips from the cartridge to the jaws of the applier, for feeding clips through the cartridge and for setting the clips about the vessel to be ligated. The handle mechanism is driven by one familiar scissors-type action within a small envelope of motion. The small motion envelope allows the applier to have a slender, elongated configuration which permits it to be used deep inside an incision site if necessary. The instrument includes elongated jaws terminating at an angle which permits the clip and the vessel to be easily observed by the surgeon as the clip is introduced about the vessel and as it is set to ligate the vessel.

The present invention includes a main handle body with a fixed anvil jaw at one end and a fixed finger ring at the other. A movable ring handle is pivotally supported on the main handle body. A movable jaw member is pivotally connected to the main handle body and includes a movable jaw tip at its forward end. The cooperative motion of the movable ring handle and the movable jaw member provides a driving force for the clip delivery and feeding mechanism supported on the handle. A cam, which is rotatably supported on the main handle body and driven by the movable ring handle, drives a pusher link in a pusher slot to provide a relatively long stroke motion for delivering clips to the jaws of the applier. Closing the movable ring handle, closes the movable jaw. Closing the movable jaw operates a ratchet link on a short motion stroke to provide a means for feeding clips through a cartridge.

The jaws of the applier are offset in a plane below the plane of the main handle body. Each of the jaws includes a U-shaped channel in which clips are guided to the tip of the jaws.

A cartridge clip fits under the applier handle in a position to permit clips to be delivered to the channels in the jaw tips. The cartridge includes a housing supporting a fixed rack and a movable rack which reciprocates in response to the short stroke motion of the ratchet link. The cartridge housing also supports a delivery element which reciprocates on a long stroke in response to the motion of the pusher link of the handle mechanism to deliver clips from the ratchet mechanism to the nose of the appliers.

The ratchet cartridge provides a compact housing for a large number of clips. As a clip reaches the end of the cartridge, it is transferred from the plane of the stationary rack to the plane directly in front of the moving rack and then to the plane of the pusher. Thus, a clip can be fed along the cartridge and advanced through three levels to the plane of the delivery element and then delivered to the nose where it may be set about a vessel.

The cartridge includes a special spring mechanism for facilitating the transfer of a clip from one level to another in the cartridge and for providing a positive indication to the user that a clip is in position ready to be delivered to the nose.

In one embodiment of the invention, the clip is merely pushed to the tip of the applier jaws. In another embodiment, the clip is positively held by the delivery element as it is being delivered from the cartridge to the tip of the jaws and continues to be held by the delivery element while the jaws are closed and the clip is set.

The preferred embodiment of the applier has been described in conjunction with clips which have a generally, V-shaped configuration with a flexible hinge at the connecting point of the two legs of the "V". These clips include outwardly extending bosses located near the end of each leg of the "V". In the embodiment of the applier where the clips are actually carried to the nose and held by the delivery mechanism while they are being set, the delivery mechanism has cooperating recesses which engage the bosses and provide a positive holding mechanism for the clip.

In the embodiment of the invention where the delivery mechanism merely pushes the clip to the jaws, the jaws themselves are equipped with recesses which receive the bosses. The clip is slightly resilient outwardly so that when the clip is slid to the nose, the bosses will engage the jaw recesses so that the clip will be held in position even after the pusher delivery element is withdrawn prior to the time that the clip is set in position.

When using a clip without bosses, the natural resilience of the clip itself helps hold the clip between the open jaws of the applier. In addition, the dimensions of the channels in the jaws of the applier are carefully controlled so that there will be a slight frictional engagement between the sides of the clip and the jaw channels to further secure the clip in the jaws.

BRIEF DESCRIPTION OF DRAWINGS

These and other advantages and features of the present invention will become apparent from the following description of certain embodiments taken in conjunction with the following drawings in which:

FIG. 1 shows an exploded perspective view of the present invention;

FIG. 1A shows a detail partial perspective of an alternative embodiment of part of the invention shown in FIG. 1;

FIG. 2 shows an exploded perspective view of an alternative embodiment of the present invention;

FIG. 2A shows a partial plan view of one element of the embodiment of FIG. 2;

FIG. 3 shows a perspective view, partially in section, of the ratchet cartridge used in conjunction with the embodiment of FIG. 1;

FIG. 4A is a schematic representation of a partial plan view of the nose area of the present invention showing the operating sequence taken along line 4A—4A in FIG. 1, with certain elements omitted for clarity, with the clip shown in elevation and the jaws shown in longitudinal section;

FIG. 4B is a sectional view taken along lines 4B—4B in FIG. 4A.

FIG. 5A is a schematic representation of a partial plan view of the nose area of the present invention showing the operating sequence taken along line 4A—4A in FIG. 1, with certain elements omitted for clarity, with the clip shown in elevation and the jaws shown in longitudinal section;

FIG. 5B is a sectional view taken along line 5B—5B in FIG. 5B.

FIG. 6A is a schematic representation of a partial plan view of the nose area of the present invention showing the operating sequence taken along line 4A—4A in FIG. 1, with certain elements omitted for clarity, with the clip shown in elevation and the jaws shown in longitudinal section;

FIG. 6B is a sectional view taken along line 6B—6B in FIG. 6B.

DETAILED DESCRIPTION OF THE PREFERRED EMBODIMENT

Referring now to FIG. 1, there is shown an exploded perspective view of the multiple clip applier of the present invention, including a handle generally designated as 10 and a cartridge 12 which is affixed underneath handle 10 and houses a number of ligating clips 11. The handle 10 operates like an elongated scissors with ring handles 2 and 4 and an elongated nose 6. The entire assembly fits conveniently into the user's hand. The elongated configuration makes it easy for the user to each into an incision to obtain access to a vessel to be ligated. The elongated nose section 6 may slightly curved to one side so that the user may more easily observe a clip as it is being applied about a vessel. Opening and closing ring handles 2 and 4 operates the mechanism of handle 10, which in turn operates the mechanism of cartridge 12 to feed a succession of clips 11 to nose section 6 where they may be set about the vessel to be ligated.

Although either metal or plastic absorbable ligating clips can be used with the multiple clip applier of the present invention, this preferred embodiment has been designed to accommodate a two-legged clip joined at the proximal end by a resilient hinge, with the first leg of the clip terminating in a deflectable hook member adapted to engage the distal end of the second leg. A suitable type of clip is disclosed in U.S. Patent Application Ser. No. 049,379 filed June 18, 1979 now abandoned, by Robert W. Mericle and assigned to the assignee of the present application. Although it has been found that clips of the kind described in this patent application work well with the multiple clip applier of the present invention, it is not intended to limit the scope of this invention to a multiple clip applier for this clip alone or for any particular kind of clip.

A description of the components of the handle mechanism will be set forth first in connection with FIG. 1. This will be followed by a description of the components of the cartridge mechanism in connection with FIGS. 1 and 3. Then the cooperative operation of the mechanisms of handle 10 and cartridge 12 will be discussed in connection with FIGS. 4, 5 and 6.

HANDLE MECHANISM

FIG. 1 shows an assembled handle 10 with an elongated configuration extending from rings 2 and 4 on the proximal end and nose 6 on the distal end. This elongated configuration permits the user to deliver clips deep into an incision. The mechanism supported on the handle provides two basic motions. The first motion is a long stroke motion for delivering clips to the jaws of the handle; the second motion is a short stroke cocking motion for advancing clips through cartridge 12.

These two motions are accomplished within the envelope of motion of the normal opening and closing of the ring handles to operate the jaws of the applier to set and deposit the ligating clip about a desired vessel.

It is important to provide these motions with a mechanism confined on the elongated configuration of the handle. The driving action is a scissors action between ring handles 2 and 4. It is important to keep the travel distance of the ring handles relatively small so that the overall slender configuration of the handle may be maintained. If the ring handles were to travel through a large distance, this is apt to make it difficult for the surgeon to use the appliers in the confined spaces of an incision site.

(a) Jaw Closing Mechanism

As shown in FIG. 1, handle 10 includes a main handle body 14 with a fixed ring handle 4 on one end and a fixed anvil jaw 16 on the other. Movable handle 18 is pivotably attached to main body 14 at pivot point 20 at one end of movable handle 18. Ring handle 2 is disposed at the other end of movable handle 18. A movable jaw 22 is pivotably attached to main handle body 14 at point 24. The distal end of movable jaw 22 incorporates a movable jaw tip 26 which moves toward anvil jaw 16 to set a clip 11. The proximal end of movable jaw 22 includes an extension lever 28 which extends past pivot point 20 of movable handle 18 in a direction toward ring handle 2. The end of extension lever 28 has a recess 27 so that it may fit flat over the other elements of the handle mechanism to maintain a reduced thickness of the handle. Extension lever 28 and movable handle 18 are aligned in such a way that movable handle 18 will engage extension lever 28 after it has moved through a predetermined angle from the fully open position of rings 2 and 4 to a partially closed position. As movable handle 18 continues to move about pivot point 20, extension lever 28 will be moved counter clockwise about pivot point 24 so as to close moveable jaw tip 26 against fixed anvil jaw 16 to set clip 11.

(b) Long Stroke Clip Delivery Motion

Cam 30 is also pivotally attached to main handle body 14 so that it may pivot about point 32. In order to reduce the thickness of the handle, cam 30 is placed in a recess 34 provided on main handle body 14. Cam 30 includes a complex cam surface 36. An extension arm 38 extending from movable handle 18 supports a cam follower bushing 40 which rides on complex cam surface 36. A pusher link 42 is pivotably connected to cam 30 at point 44. The other end of pusher link 42 supports a pusher bushing 46 which rides in pusher slot 48 which extends generally longitudinally along main handle body 14. It can be seen from FIG. 1 that as ring handle 2 closes toward ring handle 4, extension arm 38 will tend to move cam 30 clockwise about pivot point 32 so as to pull the proximal end 50 of pusher link 42 and correspondingly pusher bushing 46 rearwardly on a rather long stroke. Pusher link 42 is biased forward by a bias spring 52 connected between pivot point 44 on cam 30 and point 54 on main handle body 14 forward of the forward end of pusher slot 48. Complex cam surface 36 has a dwell portion 60 which permits movable handle 18 to continue to close after pusher bushing 46 has retracted all the way to the back of pusher slot 48. The details of this long stroke motion will be discussed more fully in connection with the operation of the apparatus later in the application.

(c) Short Stroke Clip Feeding Motion

Ratchet link 70 is pivotably connected to point 72 on movable jaw 22. The other end of ratchet link 70 is pivotably connected to ratchet bushing 74 which slides in ratchet slot 76 which runs longitudinally in main handle body 14 generally parallel to pusher slot 48. The axial length of ratchet slot 76 is much shorter than the axial length of pusher slot 48.

As movable handle 18 continues to close toward ring handle 4 after pusher bushing 46 has been almost fully retracted, movable handle 18 will engage movable jaw extension lever 28 causing pivot point 72 to rotate counter-clockwise with respect to pivot point 24. This in turn will cause ratchet link 70 to rotate clockwise about point 72 and cause ratchet bushing 74 to move rearwardly in ratchet slot 76. As movable handle 18 continues to close, movable jaw tip 26 will pivot toward fixed anvil jaw 16 and set clip 11 about the vessel to be ligated.

Movable jaw 22 is equipped with a return spring 23, one arm of which bears against the side of extension lever 28 and coils around point 54 so that the other leg extends along the side of handle body 14 and is held in position by a peg 25. When cartridge 12 is bolted to handle 10, one of the cartridge bolts projects through body 14 at point 54 to hold spring 23 in position. Thus, it will be appreciated that in the short scissors motion achieved by moving ring handle 2 toward ring handle 4, the mechanism provided on handle 10 generates a long stroke motion for pusher bushing 46 and a short stroke motion for ratchet bushing 74 and a clamping motion for setting a clip 11 about a vessel to be ligated. The sequence of these motions which permit a clip to be delivered from the cartridge 12 to the nose 6 of the appliers will be discussed in greater detail in connection with FIGS. 4 to 6.

Pusher bushing 46 and ratchet bushing 74 have been described as moving rearwardly as the ring handles 2 and 4 are closed toward one another. These bushings will move in the opposite direction when ring handles 2 and 4 are moved away from each other. Pusher bushing 46 and ratchet bushing 74 extend through pusher slot 48 and ratchet slot 76, respectively, and project below the lower surface of main handle body 14 so that they may engage the operative parts of cartridge 12.

CARTRIDGE MECHANISM

The components of cartridge 12 will now be described in connection with FIGS. 1 and 3. Cartridge 12 houses a large number of clips 11 between a reciprocating upper rack 80 and a fixed lower rack 82. Each rack is made of a flexible material, such as metal or plastic, and includes a large number of pairs of resilient fingers 84. The pairs of fingers 84 on upper rack 80 are bent downward toward the confronting surface of lower rack 82. The pairs of fingers 84 on lower rack 82 project upwardly toward the confronting surface of upper rack 80. The pairs of fingers on each rack are spaced axially apart a sufficient distance to permit a clip to rest comfortably between two adjacent pairs of fingers. As reciprocating upper rack 80 moves rearwardly, its resilient fingers will bend out of the way and slide over and then drop behind the clips on fixed rack 82. The cooperating fingers on fixed rack 82 prevent clip 11 from sliding backwards along fixed rack 82. As reciprocating rack 80 moves forward, its fingers 84 will push the clips 11 forward. The corresponding fingers on fixed rack 82 will bend out of the way and permit the clip to move forward and then snap back into position behind the advancing clip. Thus, the reciprocating motion of upper rack 80, with respect to fixed rack 82, will permit clips to be advanced along rack 82 toward the front of cartridge 12.

Fixed rack 82 is fixed into the base 86 of the generally U-shaped cartridge housing 88. The upstanding walls 90 and 92 of U-shaped cartridge housing 88 contain clips 11 for moving laterally with respect to fixed rack 82. The base 86 of cartridge housing 88 can be made of a transparent plastic so the user can easily see how many clips remain in the cartridge 12.

Reciprocating upper rack 80 is affixed to flexible strip 94, which may be made of a suitable metal or plastic. The forward end of upper rack 80 and strip 94 include cooperating "V" shaped recesses 96 and 98 configured to conform to the shape of a clip 11. Recesses 96, 98 permit reciprocating upper rack 80 to push the last clip forward while still maintaining the clip in a partially open configuration. The clip chosen to be illustrated in this application is a two-legged clip joined by a flexible hinge and carried in the cartridge in a partially open position, as shown best in FIG. 6A. The V-shaped recess 96, 98 mates with the back of the V-shaped clip so that the clip may be forced forward without tending to open the clip. If the clip were opened as it was moved forward, it would have a tendency to jam against the sidewalls 90 and 92 of the cartridge housing 88.

The flexible strip 94 and reciprocating upper rack 80 are placed together between the walls 90 and 92 of cartridge housing 88. It will be observed, particularly in FIGS. 1 and 3, that the inward upper edge of each sidewall 90 and 92 includes a groove, or rabbet 100, extending axially from the rearward face of cartridge housing 88 to a shoulder 102. A pusher 110 fits into cartridge housing 88 on top of strip 94 and slides in grooves 100. Pusher 110 includes a rearward body section 112 whose edges fit in grooves 100 and intermediate section 114 of a narrower transverse dimension and forwardly extending fingers 116. Intermediate section 114 is separated from body section 112 by a stop 118 which tapers inwardly so that intermediate section 114 has a reduced transverse dimension which will permit it to slide between walls 90 and 92 until stop 118 abuts against shoulder 102.

As will be explained in greater detail in connection with FIGS. 4 to 6, fingers 116 extend beyond the distal end of cartridge housing 88 when stop 118 is against shoulder 102 so that the end of the fingers extends into the nose section 6 of the handle to push a clip between fixed anvil jaw 16 and movable jaw tip 26 into a position where the clip is ready to be applied about a vessel. The fingers are slender so that they may flex in response to the contour of jaws 16 and 26. The forward edges of fingers 116 are tapered to form a "V" of the same angle as the "V" formed by the two legs of the clip. This permits the fingers to push the clip forward into the nose without opening the clip. As discussed previously in explaining the "V" recesses 96 and 98 at the front of reciprocating upper rack 80, it is important to prevent clip 11 from opening too much as it is moved from cartridge housing 88 to nose section 6 so that it will not jam as it travels through this distance. The lateral edges of fingers 116 may be trimmed between intermediate section 114 and the end of the fingers, i.e., in area 122, to provide greater resiliency to fingers 116.

U-shaped cover 130 fits over the outside of walls 90 and 92 of cartridge housing 88 to enclose reciprocating upper ratchet 80, strip 94 and pusher 110 and the clips 11 within housing 88. Cover 130 is held in position by a number of screws 132 which fit through clearance holes 134 in the cover and screw into tapped holes 136 in cartridge housing 88. The assembled cartridge 12 is affixed to the underside of housing 10 by a number of screws 140 projecting through clearance holes 142 in feet 144 projecting from sidewalls 90 and 92. Screws 140 screw into tapped holes 146 on main handle body 14. One of these screws 140 is used to anchor pusher link bias spring 52 for pusher link 42 and movable jaw return spring 23 for movable jaw 22. Cover 130 may be provided with recesses 138 to accommodate feet 144.

INTERACTION OF HANDLE & CLIP MECHANISMS

The driving mechanism for pusher 110 and for reciprocating upper rack 80 will now be described. Upper rack 80 is affixed to strip 94. Bolt 150 projects through hole 152 in strip 94, through ratchet bushing 74, through ratchet slot 76, in main handle body 14 and through ratchet link 70. Bolt 150 is held in ratchet link 70 by washer 154 and nut 156. Thus, as ratchet link 70 reciprocates in ratchet slot 76 as ring handles 2 and 4 open and close to activate the handle mechanism, reciprocating upper rack 80 will reciprocate back and forth to advance clips 11 through cartridge 12.

Bolt 160 extends through hole 162 at the back of pusher 110 through pusher bushing 46, through pusher slot 48 and into the forward end of pusher link 42. Bolt 160 is held in position in pusher link 42 by means of washer 164 and nut 166. Thus, as pusher link 42 moves back and forth in pusher slot 48 under the influence of the handle mechanism, pusher 110 will likewise move back and forth to advance clips from cartridge 12 into nose section 6 of handle 10. The body section 112 of pusher 110 includes an axial slot 170 wide enough and long enough to permit pusher 110 to move free from any interference with ratchet bushing 74 so that reciprocating upper rack 80 and pusher 110 can traverse their respective motions without interfering with one another. Similar slots 172 and 174 are provided in cartridge cover 130 so that pusher bushing 46 and ratchet bushing 74 may move without interfering with cover 130. Still referring to FIGS. 1 and 3, a description of a spring mechanism at the forward end of cartridge 12 will now be set forth. Projecting from the ends of sidewalls 90 and 92 of U-shaped cartridge housing 88 are two extension arms 180 and 182. Arms 180 and 182 extend generally parallel to sidewalls 90 and 92. The base 86 of U-shaped cartridge housing 88 does not extend along with extension arms 180 and 182 so that base 86 of cartridge housing 88 is open between extension arms 180 and 182. The tips 184 of arms 180 and 182 expand in a slight taper from point 186 to the end of arms 180 and 182. A spring mechanism is supported between the ends 184 of arms 180 and 182 to deliver the clip from the plane of rack 82 to the plane of pusher 110 within cartridge 12. This spring mechanism includes a transverse connector 190 extending between tips 184 of extension arms 180 and 182 and fixed between the arms. The height of connector 190 is slightly less than the height of arms 180 and 182 so that pusher fingers 116 may slide over the top of connector 190 to pick up a clip and push it into the nose section 6 of handle 10. The edge of connector 190 facing rack 82 is chamfered to facilitate free motion of clip 11 over connector 190 without catching. A strip of spring material 194 is fixed to the bottom of connector 190, for example by means of screws 195, and projects into the space between the distal end of cartridge 86 and the confronting surface of connector 190. A transfer wedge 196 is affixed to the projecting end of spring material 194 by means of screws 197. Spring material 194 may be spring steel or a suitable resilient plastic.

Transfer wedge 196 is thin at the surface adjacent the end of rack 82 and thick at the surface adjacent chamfered edge 192 of connector 190. This wedge shape facilitates the transfer of a clip from the plane of rack 82 to the plane of pusher 110 so that it may be more easily delivered to nose 6 of handle 10. Rack extension 198 is bonded to the top surface of transfer wedge 196 and includes fingers 200 to prevent clip 11 from sliding off transfer wedge 196 or being forced off as pusher 110 retracts, as will be subsequently explained in connection with FIGS. 4 to 6.

Still referring to FIG. 1, some details of the construction of handle 10 and the way in which cartridge 12 fits against handle 10 to permit clips to be fed to nose section 6 will now be discussed. All of the pivot point of the handle mechanism are provided with suitable bushings to provide low friction action for the mechanism. Movable handle 18 is connected to main body 14 at pivot point 20 by means of a machine screw 201 which extends through bushing support hole 202 and bushing 204 mounted in hole 202 and which is then threaded into tapped hole 206 on main body 14. Cam 30 is supported to pivot about pivot point 32 by means of screw 210 which extends through bushing support hole 212 and bushing 214 mounted in hole 212 and which is then threaded into tapped hole 216 in main body 14. Pusher link 42 is connected to pivot about point 44 by means of screw 220 which extends through bushing support hole 222 and bushing 224 mounted in hole 222 and which is then threaded into tapped hole 226 on cam 30. Link 70 is connected to pivot about pivot point 72 by means of screw 230 which extends through bushing support hole 232 and bushing 234 in hole 232 and which is then threaded into tapped hole 236 in movable jaw 22.

Extension arm 38 is constrained to move on complex cam surface 36 by means of screw 240 projecting past cam surface 36 and through cam follower bushing 40 and into tapped hole 246 in extension arm 38. Movable jaw 22 is supported to pivot about point 24 by means of machine screw 250 which projects through bushing support holes 252 and 253 into bushing 254 which bushing 254 contains tapped hole 256 into which machine screw 250 is threaded.

FIG. 1 shows that nose section 6 is stepped below the plane of main handle body 14 and curves away from the plane of main handle body 14. Step 280 drops movable jaw 26 below the plane of main handle body 14. Step 282 drops the plane of anvil jaw 16 below the plane of main handle body 14 so that jaws 16 and 26 are aligned with one another. Jaws 16 and 26 have oppositely facing U-shaped channels 284 and 286 for receiving clips 11. It can be seen that the entrance to U-shaped channel 286 is dropped sufficiently below the plane of main handle body 14 to permit pusher 110 to extend directly into channels 284 and 286 from cartridge 12. The end of jaws 16 and 26 must be adapted to conform to the geometry of the clip, for example, the clip which has been chosen to illustrate the preferred embodiment of this multiple clip applier has raised bosses 290 (see FIG. 6A) on each of its legs which engage corresponding depressions 292 (see FIG. 6A) at the tip of each jaw. The raised bosses 290 are located near the end of each leg and face outwardly in the plane defined by the "V" shaped clip. Pusher 110 pushes the clip forward into the jaws until bosses 290 drop into depressions 292.

The channels 284 and 286 have a constant width such that the clip may slide easily out to the end of the jaws 16 and 26. However, the jaws are configured so that in the fully open position, the jaws taper slightly toward one another so that the transverse dimension from the base of channel 286 and movable jaw tip 26 and channel 284 in anvil jaw 16 decreases as a clip proceeds toward the tips so as to partially close the clip as it is delivered to the end of the jaws. This has the advantage of using the spring action of the clip itself to assist in holding the clip in the jaws and also to partially close the clip so that less motion is required on the part of the user to completely close and set the clip about a vessel.

Cover 130 supports bolt 176 which projects through hole 177 to support circular guide 178 between fingers 116 of pusher 110. Fingers 116 flex toward one another when they deliver a clip to nose section 6. Guide 178 returns the fingers to their separate position when pusher 110 is retracted so that the tips 120 of fingers 116 will be returned to the correct position for picking up the next clip. Since pusher 110 and fingers 116 are made of plastic, this guide 178 is necessary to make sure that the tips 120 return to their correct position if, after a number of operations, the resiliency of the plastic of which fingers 116 are made begins to dissipate.

PROGRESSION OF A CLIP THROUGH THE CARTRIDGE

The progression of a clip from the plane of fixed rack 82 onto transfer wedge 196 up to the plane of pusher 110 and out through the nose section 6 of the handle will now be traced in connection with FIGS. 4, 5 and 6. With jaws 16 and 26 all the way open and correspondingly ring handles 2 and 4 all the way open, pusher link 42 will be at the forward point in pusher slot 48 so that fingers 116 of pusher 110 will be extended all the way into the channels 284 and 286, depositing a clip 11 at the end of nose section 6 ready to be set about a vessel as shown in FIG. 4A. With the ring handles 2 and 4 all the way open, movable jaw 22 will be urged by its bias spring 23 to its most open position so that ratchet link 70 and its ratchet bushing 74 will be all the way forward in ratchet slot 76. With ratchet bushing 74 all the way forward, V-shaped recess 98 at the forward end of reciprocating upper rack 80 will be aligned with the forward portion of fixed rack 82. In the plan view shown in FIG. 4A, a small portion of fixed rack 82 can be seen through V-slot 98 in reciprocating upper rack 80. With the mechansim in this position, a second clip 11 rests on rack extension 198 held in position by fingers 200.

As can be seen best in FIG. 4B, the clip resting on rack extension 198 is forced against body portion 112 of pusher 110 causing spring 194 to deflect so that transfer wedge 196 tends to deflect below the surface of cartridge 12. This deflection is observable by the user and serves as an indicator to tell the user that a clip is in position on rack extension 198, ready to be placed in front of the pusher fingers 116 when pusher 110 is withdrawn.

As one starts to close ring handle 2 toward ring handle 4, extension arm 38 of movable handle 18 will cause cam 30 to pivot clockwise about cam pivot point 32 so as to move pusher link 42 rearwardly in pusher slot 48 and correspondingly to retract pusher 110 out of nose 6 of handle 10, leaving clip 11 at the tip of jaws 16 and 26 in the open position. The curved configuration of nose section 6 offsets the tip of nose 6 so that the clip may be more easily seen by the user when the clip is in position ready to be closed around the vessel.

When pusher bushing 46 is almost all the way to the back of pusher slot 48, the forward portion of moving handle 18, between pivot point 20 and extension arm 38, engages extension lever 28 of movable jaw 22 and starts to close movable jaw tip 26 toward anvil jaw tip 16 and close a clip about a vessel. At this point, pivot point 72 of ratchet link 70 rotates counter-clockwise and causes ratchet bushing 74 to move rearwardly in ratchet slot 76 and correspondingly move reciprocating rack 80 backwards.

Thus, for the final part of the closing motion when movable jaw tip 26 moves toward anvil jaw 16 to set a clip, both pusher 110 and reciprocating rack 80 are moving backwards together. When pusher bushing 46 is all the way back in pusher slot 48, cam follower bushing 40 enters dwell portion 60 of complex cam surface 36 so that ring handle 2 may continue to close toward ring handle 4 without jamming pusher bushing 46 against the back of pusher slot 48.

The completely closed position of the nose section can be seen in FIGS. 5A and 5B. It will be noted, particularly in FIG. 5A, the jaws never come completely together so that any tissue which may migrate between the jaw tips will not be severed. It will also be noted in FIG. 5B that in the completely closed position, the end of fingers 116 are aligned with the end of fixed rack 82. The clip that had been compressed between transfer wedge 196 and body portion 112 of pusher 110 moves up into the plane of pusher 110 as pusher 110 withdraws behind the end of transfer wedge 196. At the same time, reciprocating upper rack 80 has withdrawn rearwardly of the forward end of fixed rack 82 a distance equal to about one clip length. The resilient finger pairs 84 extending from movable rack 80 flex easily out of the way as movable rack 80 moves backwards. When these flexible fingers clear the rear end of the last clip on fixed rack 82, the fingers will spring back behind that clip. The corresponding resilient finger pairs 84 on fixed rack 82 prevent the the remaining clips from being drawn rearwardly as reciprocating upper rack 80 retracts.

It can now be appreciated why rack extension 198 requires retention fingers 200 to hold the clip on transfer wedge 196. It is desirable to retract pusher 110 quickly. Since the clip is wedged between pusher 110 and transfer wedge 196, it is likely that the clip will be drawn rearwardly with pusher 110 if it moves back quickly. Retention fingers 200 prevent this clip from moving backwards when pusher 110 is retracted.

A clip has now been transferred from the plane of the fixed rack 82 to the plane of pusher 110 ready to be thrust forward into the nose 6.

The user will now start to open the handles after the clip has been set about a vessel so that the clip may be released from jaws 16 and 26. As the user begins to open ring handle 2 away from ring handle 4, cam 30 will begin to pivot in the counter-clockwise direction about pivot point 32 so as to drive pusher link 46 forward in pusher slot 48 and correspondingly to drive pusher 110 forward into nose section 6. It can be seen from FIGS. 5B and 6B that as the pusher moves forward, it will pick up the next clip and deliver it toward the nose. It will also be seen from FIG. 1 that as ring handle 2 moves away from ring handle 4, movable handle 18 will begin to disengage from lever extension 28 of moving jaw 22 so that pivot point 72 of ratchet link 70 will move in the counter-clockwise direction, thus drawing ratchet bushing 74 forward in ratchet slot 76 and correspondingly moving reciprocating ratchet 80 forward to a point where recess 98 at the end of ratchet 80 is aligned with the end of fixed rack 80. The forward motion of reciprocating rack 80 will drive the last clip from fixed rack 82 onto rack extension 198 and against the forward moving pusher 110 so as to deflect transfer wedge 196 against spring 194 so that the sequence will repeat itself again.

It can be seen that a plurality of clips may be advanced forward through cartridge 12 to the nose section 6 of handle 10. The clips may be set in rapid succession to ligate a large number of vessels quickly and efficiently without having to remove the applier from the wound to grasp each additional clip in the clip appliers.

The last clip in each cartridge is a lockout clip especially designed to jam the mechanism to provide an indication to the user that the cartridge is empty. The lockout clip is a rigid metal clip which will advance only into the beginning of channels 284 and 286 of jaws 16 and 26. If pusher 110 attempts to push this rigid metal clip further into the jaws, the lockout clip will bind. This specially designed lockout clip is also colored a different color from the remainder of the clips so that the user can easily observe through transparent housing base 86 that he is using the last clip.

Alternatively, fixed rack 82 may be replaced with fixed rack 300, shown in FIG. 1A, and spring 194, bolts 195, transfer wedge 196 and extension rack 198 which form the spring mechanism for shifting a clip from the plane of fixed rack 82 to the plane of moving rack 80 may be eliminated. Alternative fixed rack 300 includes a projection 302 extending between extension arms 180 and 182 toward connector 190, and terminating in a curved deflector 304. The transverse dimension of projection 302 is less than that of alternative rack 300 so that projection 302 will easily flex as a clip is moved onto projection 302 toward deflector 304. The deflector works in the same fashion as the transfer wedge 194 in the embodiment shown in FIG. 1 and serves to force a clip against the body portion 112 of pusher 110. When pusher 110 is fully retracted, deflector 304 will deliver the clip to the plane of the tips 120 in front of fingers 116 of pusher 110 ready for delivery to the nose section 6 of handle 10. Alternative rack 300 is otherwise the same as fixed rack 82 and has the same plurality of finger pairs 84 which function in the same way as with the embodiment of FIG. 1.

In an alternative embodiment, shown in FIG. 2, the drive mechanism housed on the handle body is differently arranged to provide a slightly different motion for delivering the clip to the jaws. This difference is occasioned by the use of a different kind of mechanism to deliver the clips to the jaws. Instead of pushing the clip into the jaws and retracting the pusher before the clip is set about the vessel to be ligated, the clip is actually carried to the jaws and the carrier remains at the tip of the jaws while the clip is being set.

Referring now to FIG. 2, handle 500 is very similar to handle 10 shown in FIG. 1. However, cam 30 is replaced by cam 530 which pivots about point 532 so that as handle ring 502 closes toward handle 504, cam 530 will rotate counter-clockwise about point 532, thus, driving carrier link 542 forward toward the jaws of the applier as the handles close. The dwell surface 560 on cam 530 is designed so that carrier link 542 and correspondingly carrier bushing 546 will stay forward in carrier slot 548 as the handles continue to close and clamp movable jaw 526 against anvil jaw 516 to set a clip about a vessel to be ligated.

Ratchet link 570 operates the same way as ratchet link 70 of the embodiment shown in FIG. 1. It can also be seen in FIGS. 2 and 2A that pusher 110 of the embodiment shown in FIG. 1 has been replaced by carrier 510 which is similar in all respects to pusher 110 except that the tips 520 of fingers 516 are configured to hold a clip while it is being advanced to the jaws. If, for example, the bossed clip previously mentioned in this application is used with carrier 510, it can be seen in FIG. 2A that bosses 290 fit conveniently into recesses 513 in the end of tips 520. Recess 514 is designed to accommodate one leg of clip 11 and arched surface 515 is designed to accept the other end of clip 11.

The spring mechanism used to transfer clips from the plane of the fixed rack to the plane of carrier 510 is different from that used with the embodiment of FIG. 1. Rack extension 198 is eliminated and the shape of transfer wedge 196 and connector 190 is modified so that in plan view, their projections appear as generally complimentary trapezoids. As shown in FIG. 2, this is accomplished by tapering the confronting surfaces of modified transfer wedge 596 and modified connector 590. This trapezoidal shape of modified transfer wedge 596 and modified connector 590 permit the forward faces of clip 11 to rest against the confronting face 591 of modified connector 590 so that the clip will be positioned properly as it leaves the fixed rack for easy entry into recesses 513, 514 and 515 at the end of carrier 510. For different shaped clips, the shape of modified transfer wedge 596, connector 590 and the configuration of the end 520 of carrier 510 may be modified to suit the particular clip involved.

In operation, the alternative apparatus shown in FIG. 2 is very similar to that of the apparatus shown in FIG. 1. As ring handle 502 is moved from the fully opened position toward ring handle 504, carrier link 542 and correspondingly carrier bushing 546 will move carrier 510 forward to pick up a clip from modified transfer wedge 596 and carry it to the end of the jaws.

As ring handle 502 continues to close, jaw 526 will chose toward anvil jaw 516 and set the clip. While the clip is being set, the clip is held in the recesses 513, 514 and 515 at the end of carrier 510. Closing jaws 526 and 516 activates ratchet link 570 and correspondingly ratchet bushing 574 to draw reciprocating upper rack 80 backwards behind the last clip on fixed rack 82. After the clip has been set and ring handle 502 begins to open away from ring handle 504, ratchet link 570 will permit upper rack 80 to move forward and advance the next clip onto modified transfer wedge 596. Further opening of ring handle 502 will retract carrier 510 out of the nose and all the way back behind the clip on modified transfer wedge 596 so that the spring action of spring 194 will force the clip into recesses 513, 514 and 515 at the end of carrier 510. Cam 530, movable handle 518, carrier link 542 and carrier slot 548 are synchronized with the travel of carrier 510 so that recesses 513, 514 and 515 are properly aligned with the clip on modified transfer wedge 596 when carrier 510 is fully retracted so that the clip will move easily into these recesses. Thus, the clip will be in position, ready to be delivered to the nose the next time the ring handles 502 and 504 are closed.

Carrier housing 588 is different from carrier housing 88 in that slot 100 extends the entire length of the housing and stop 102 is eliminated. Also, carrier 510 does not have a shoulder like shoulder 118 of pusher 110. This stop and shoulder in the embodiment of FIG. 1 act as a positive stop for the forward motion of pusher 110. Since carrier 510 extends all the way into the nose of handle 10 and holds the clip while it is being set, there is no need for a stop in the embodiment of FIG. 2.

Thus, it can be seen that the present invention provides apparatus for applying a large number of ligating clips in rapid succession. The apparatus includes a handle to which a multi-clip cartridge is affixed. The handle houses a mechanism which operates to provide a long stroke motion for delivering clips to the nose and a short stroke motion for feeding clips through the cartridge, driven by a familiar scissors action in a small motion envelope. The handle has an elongated shape to permit the surgeon to use the apparatus deep within a wound and an elongated curved nose to make it easier to see the clip as it is being delivered to the nose and as it is being set about a vessel. Even though the apparatus provides good visibility for the clip, it also holds the clip firmly in the instrument while the clip is being advanced through the cartridge, transferred to the entry to the nose and delivered to the tip of the nose for setting.

The clip cartridges used with the handle fit conveniently into a position on the handle for easy assembly and manufacture. The cartridge can be transparent so that the user can see how many clips are left. A displaceable spring-feed mechanism gives the user a positive indication that a clip is in position, ready to be delivered to the nose. The cartridge employs an efficient ratchet mechanism which is not overly sensitive to manufacturing tolerances. The cartridge can be equipped with different means for delivering the clip to the jaws. The clip may be pushed forward and deposited in the jaws, and bosses on the clip may be engaged by cooperating recesses built into the jaws. Alternatively, the clip may be carried to the tips of the jaws and held there while it is being set. The recesses to cooperate with the clip bosses are built directly into the carrier itself.

While the present invention has been described in connection with certain preferred embodiments, those skilled in the art will appreciate that certain modifications may be made without departing from the scope of the present invention. It is, therefore, not intended that the present invention be limited except as set forth in the following claims.

We claim:

1. A scissors-type medical instrument for sequentially applying a plurality of ligating clips comprising:
   first and second jaws disposed in confronting relationship at the distal end of said instrument and adapted to be pivoted together by the scissors action of the instrument to hold and set a ligating clip;

first and second scissors handles operatively connected to said jaws to open and close said jaws;

bias means biasing said handles and said jaws in a fully open position when said instrument is at rest;

a mechanism disposed between the jaws and the handles;

said mechanism including means for providing a reciprocating long-stroke motion for delivering successive clips to the jaws, said long-stroke motion means acting initially proximally as said handles are closed from said biased, fully-open rest position to a fully-closed position, and said long-stroke motion means then returning distally only under the influence of said bias means so that a clip rests between said jaws, ready to be applied to a ligating site, when said long-stroke motion means is at rest; and, said mechanism further including means synchronized with said long-stroke motion means for providing a reciprocating short-stroke motion for feeding clips in succession;

said mechanism providing the motion to feed a successive clip into position for advancement to said jaws during the normal closing of said first and second scissors handles from said rest position and to automatically deliver a succeeding clip to said jaws, ready for setting, only under the influence of said bias means as said first and second of the scissors handles return to said fully-open rest position.

2. The instrument of claim 1 further including an elongated handle body having a distal end and a proximal end, said first scissors handle integrally attached to said proximal end and said first jaw integrally attached to said distal end;

a movable handle pivotably connected to said handle body;

a movable jaw member pivotably connected to said handle body, said second jaw integrally attached to said distal end of said movable jaw, an extension lever extending proximally from a proximal portion of said movable jaw member, said extension lever aligned to engage said movable handle as said movable handle closes toward said first handle;

the pivot points of said movable jaw member and said movable handle being disposed on said handle body so that the scissors handles move from a fully open position to a partially closed position before said movable jaw extension lever and said movable handle engage to close the jaws.

3. The instrument of claim 2 further including:

an extension arm extending from said movable handle in the plane of said first and second scissors handles over said handle body;

a cam pivotably mounted on said handle body and having a cam surface operatively engaging said extension arm;

a delivery slot in said handle body;

a delivery link having a first end pivotably connected to said cam and having a second end operatively engaging said delivery slot, said extension arm and said cam cooperating to drive said delivery link in a reciprocating long stroke motion toward and away from said jaws as said handles are opened and closed; and, spring bias means for biasing said delivery link toward said jaws.

4. The apparatus of claim 3 further including a delivery bushing extending from said second end of said delivery link through said delivery slot to the opposite side of said handle body.

5. The instrument of claim 3 wherein said cam includes a slot providing a complex cam surface having a first portion and a second portion;

the first portion of said complex cam surface providing controlled long stroke motion for said delivery link in response to a first part of the opening or closing of said scissors handles;

the second portion of said complex cam slot providing a dwell so that said delivery link will remain stationary in response to a second part of the opening and closing of the scissors handles.

6. The instrument of claim 2 further including a ratchet slot in said handle body;

a ratchet link having one end pivotably connected to said movable jaw member and having the other end operatively engaging said ratchet slot, said movable jaw extension lever and said movable handle cooperating to drive said ratchet link in a reciprocating short stroke motion toward and away from said jaws as said handles are opened and closed;

the shape of said cam surface and the pivot points of said cam, said movable handle and said movable jaw member being positioned to synchronize the long stroke motion of said delivery link and the short stroke motion of said ratchet link with the opening and closing of the jaws;

second spring bias means for biasing said ratchet link toward said jaws.

7. The instrument of claim 6 further including a ratchet bushing extending from said second end of said ratchet link through said ratchet slot to the other side of said handle body.

8. The instrument of claim 1 further including a cartridge of ligating clips disposed adjacent the plane of motion of said mechanism and including a number of clips arrayed in a line from the first position adjacent said jaws for a desired number of positions extending rearwardly from said jaws toward said handles;

an elongated delivery means disposed in said cartridge and aligned between said clips and said mechanism and adapted to reciprocate in response to said long stroke motion means for delivering a clip from said first position to said jaws;

ratchet means disposed in said cartridge and operatively engaging said plurality of clips and adapted to reciprocate in response to said short stroke motion means to feed said clips to said first position.

9. The apparatus of claim 8 wherein said jaws are offset below the plane of said handle and aligned with said delivery means;

each of said jaws having a U-shaped channel disposed in confronting relationship for receiving said clip and said delivery means and for holding said ligating clip as it is being applied.

10. The apparatus of claim 9 wherein said U-shaped channels are slightly tapered toward one another in a direction advancing distally along said U-shaped channels when said jaws are in the fully open position.

11. The instrument of claim 8 wherein said jaws are slightly curved away from the plane of said handles to provide a greater visibility for the tip of the jaws and for a clip while it is being applied.

12. The instrument of claim 11 wherein said delivery means is flexible to accommodate the curve of said jaws as said delivery means is inserted into the jaws.

13. The instrument of claim 8 wherein said delivery means includes axially extending flexible fingers having tips and wherein each tip is tapered to conform to the shape of the confronting clip so that said delivery means may push said clip into said jaws;

the synchronized motion of said long stroke motion means adapted to push a clip to the end of the jaws as the handles are fully opened and to fully retract the delivery means as the handles move from the fully open to a partially closed position before the jaws begin to close.

14. The instrument of claim 8 wherein said delivery means includes axially extending fingers having tips;

said finger tips including recesses for receiving and holding a clip while it is delivered to said jaws and while said jaws are closed to apply the clips;

the synchronized motion of said delivery means synchronized to fully retract the delivery means when the scissors handles are fully opened and to carry said clip to the end of said jaws as the scissors handles are moved from the fully opened to the partially closed position before the jaws are closed and to hold the delivery means in the jaws while the jaws are being closed to apply the clip;

said jaws closing directly on said finger tips and moving said finger tips together to close said clip.

15. A scissors-type medical instrument sequentially applying a plurality of ligating clips comprising:

an elongated handle body having a distal end and a proximal end;

a first scissors handle integrally attached to said proximal end of said handle body;

a first jaw integrally attached to said distal end of said handle body;

a movable handle pivotably connected to said handle body;

a movable jaw member pivotably connected to said handle body, a second jaw integrally attached to the distal end of said movable jaw member;

an extension lever extending proximally from a proximal portion of said movable jaw member, said extension lever aligned to engage said movable handle as said movable handle closes toward said first scissors handle;

the pivot points of said movable jaw member and said movable handle being disposed on said handle body so that the handles move from a fully-open position to a partially closed position before said movable jaw extension lever and said movable handle engage to close said jaws;

a mechanism disposed between said jaws and said handles operating in the plane of the handles and driven by the normal opening and closing action of said first scissors handle and said movable handle and including:

means for providing a reciprocating long-stroke motion for delivering clips to the jaws; and, means synchronized with said long-stroke motion means for providing a reciprocating short-stroke motion for feeding clips in succession whereby said means provides the motion to feed a successive clip into position for advancement to said jaws during the normal closing of said first and second scissors handles from said rest position and to automatically deliver a succeeding clip to said jaws, ready for setting, only under the influence of said bias means as said first and second of the scissors handles return to said fully-open rest position.

* * * * *